United States Patent [19]

Akiyama et al.

[11] 4,238,359

[45] Dec. 9, 1980

[54] PROCESS FOR PREPARING SPHERICAL SHAPED PELLETIZED OXIDE CATALYSTS COMPRISING MOLYBDENUM AND PHOSPHORUS

[75] Inventors: Shinichi Akiyama; Haruhisa Yamamoto; Nobuaki Yoneyama; Shinji Matsumoto, all of Takaoka, Japan

[73] Assignee: Nippon Zeon Co. Ltd., Tokyo, Japan

[21] Appl. No.: 38,057

[22] Filed: May 11, 1979

Related U.S. Application Data

[60] Division of Ser. No. 940,484, Sep. 7, 1978, abandoned, which is a continuation of Ser. No. 623,616, Oct. 20, 1975, abandoned.

[30] Foreign Application Priority Data

Oct. 23, 1974 [JP] Japan ................................ 49/121418

[51] Int. Cl.$^3$ ........................ B01J 21/18; B01J 21/14; C07C 51/25; C07C 57/04
[52] U.S. Cl. .................................... 252/437; 252/435; 252/448; 562/532; 562/534; 562/535
[58] Field of Search ...................... 252/435, 437, 448; 264/117; 562/532, 534, 535

[56] References Cited

U.S. PATENT DOCUMENTS

| | | | |
|---|---|---|---|
| 3,661,801 | 5/1972 | Gutmann et al. | 252/435 |
| 3,795,703 | 3/1974 | Niina et al. | 562/535 |
| 3,956,377 | 5/1976 | Dolhyn et al. | 562/535 |
| 3,976,688 | 8/1976 | Akiyama et al. | 562/535 |
| 4,077,912 | 3/1978 | Dolhyj et al. | 252/477 R |

*Primary Examiner*—P. E. Konopka
*Attorney, Agent, or Firm*—Sherman & Shalloway

[57] ABSTRACT

A catalyst composition for use in preparing unsaturated carboxylic acids by the vapor-phase oxidation of unsaturated aldehydes, said catalyst composition comprising an oxide composition containing as essential ingredients (1) phosphorus, (2) molybdenum and (3) X in which X is at least one element selected from the group consisting of thallium and metals of Groups IA and II of the periodic table, characterized in that said oxide composition has a surface area of 4 to 20 m$^2$/g and a pore volume of 0.08 to 0.5 ml/g, whereby said catalyst composition has an excellent reproducibility of catalytic activity and a process for preparing aforesaid catalyst composition.

10 Claims, No Drawings

PROCESS FOR PREPARING SPHERICAL SHAPED PELLETIZED OXIDE CATALYSTS COMPRISING MOLYBDENUM AND PHOSPHORUS

This is a division of application Ser. No. 940,484, filed Sept. 7, 1978 which in turn is a continuation of application Ser. No. 623,616 filed Oct. 20, 1975, both now abandoned.

This invention relates to a catalyst composition for the vapor-phase oxidation of unsaturated aldehydes which has superior reproducibility of catalytic activity, and to a process for preparing the catalyst composition.

Generaly, for use in various chemical reactions, it is very important to prepare catalysts having the same level of activity (in other words, always giving the same reaction result) with good reproducibility. As is well known, however, the desired reproducibility is frequently not obtained. This is also experienced in the field of catalysts for oxidizing unsaturated aldehydes to which the present invention pertains. Usually, these oxidation catalysts are composed of catalytically active substances alone and used as such, or prior to use, these substances are supported on a carrier such as silica, alumina, silicon carbide or diatomaceous earth or diluted with a finely divided carrier. In either case, the resulting catalysts do not always exhibit the same or similar activities.

In the oxidation reaction of unsaturated aldehydes utilizing reaction apparatuses of the fixed bed or moving bed type, the catalyst is used in the form of pellets of a suitable size. Such a pelletized catalyst is produced by molding on a tabletting machine, extruder, conical pan pelletizer or tumbling granulator, etc., but in many cases, it is difficult to prepare the catalyst without reducing its catalytic activity. Furthermore, even when the production of such pellets follows a certain specified manual so as to use the same operational procedure, the resulting catalysts pellets frequently differ in catalytic activity from batch to batch (usually, the resulting catalysts have a lower catalytic activity than expected). The possible causes of this are the chemical change of the catalyst, the change of its shape, and the influences of its surface area and pore volume or of a lubricant or binder, which may occur during the preparation of pelletized catalysts from powdery starting materials. But since they also relate to a particular reaction in which the catalyst is used, no definite theory has ever been established for ascertaining them.

The term "pellets," as used in the present application, is meant to include those of pillar-like, tablet-like, annular and spherical shapes.

For the preparation of unsaturated carboxylic acids such as acrylic acid or methacrylic acid by the vapor-phase oxidation of unsaturated aldehydes such as acrolein or methacrolein, oxide compositions containing as essential ingredients (1) phosphorus, (2) molybdenum and (3) X (X being at least one element selected from the group consisting of thallium and metals of Groups IA and II of the periodic table) (to be referred to sometimes as P-Mo-X oxide composition) have been known as catalysts having superior catalytic activity and a long active lifetime (see, for example, U.S. Pat. Nos. 3,795,703 and 3,882,047, Japanese Laid-Open Patent Publications Nos. 82013/75, 83321/75, 83322/75, 84517/75, 84519/75 and 84520/75, and Japanese Patent Applications Nos. 29405/74, 29406/74 and 85763/74).

These P-Mo-X oxide compositions inherently show superior activity, but when they are pelletized by the pelletizing machines, their catalytic activity is sometimes reduced. Or even when they are molded by the same method, it is sometimes impossible to obtain catalysts having the same or similar activities. Accordingly, in order to employ the above oxide compositions as commercially feasible catalysts, it has been necessary to improve them further in regard to the reproducibility of their catalytic activity.

It is an object of this invention therefore to provide a catalyst composition having an excellent reproducibility of its catalytic activity.

Another object of this invention is to provide a process for preparing catalyst compositions having the same level of activity with good reproducibility.

We have made an extensive investigation of the cause of changes in catalytic activity which often occur at the time of producing catalyst pellets by molding the P-Mo-X oxide composition using molding machines. Unexpectedly, we have found that the main cause of this is not the change of the catalyst shape ascribable to the difference of the molding method nor the chemical change of the catalyst incident to press-molding, but comes from the fact that the fine pores of the catalyst change at the time of molding and this change causes changes in the surface area and pore volume of the catalyst. Based on this information, we tried to find out conditions for obtaining P-Mo-X oxide composition catalysts which have always good reproducibility of catalytic activity irrespective of the method of catalyst molding. This finally led to the discovery that these oxide compositions should have a surface area of 4 to 20 $m^2/g$, preferably 4.5 to 20 $m^2/g$, more preferably 4.5 to 15 $m^2/g$ and a pore volume of 0.08 to 0.5 ml/g, preferably 0.09 to 0.5 ml/g, more preferably 0.09 to 0.35 ml/g.

According to the present invention, therefore, there is provided an oxide composition comprising (1) phosphorus, (2) molybdenum and (3) X (X being the same as defined above) as essential ingredients and having a surface area of 4 to 20 $m^2/g$ and a pore volume of 0.08 to 0.4 ml/g as a catalyst composition for the vapor-phase oxidation of unsaturated aldehydes such as acrolein or methacrolein to unsaturated carboxylic acids such as acrylic acid or methacrylic acid which have an excellent reproducibility of catalytic activit and can always give superior reaction results.

The surface area of the oxide composition is measured by the BET method (Brunauer Emmet Teller method) in which the measurement is made using a nitrogen gas ($-195.8°$ C.) as an adsorption seed after deaeration for 1 hour at 200° C. The pore volume is measured by totalling the volumes of pores with a size of 35 Å to 120 microns in accordance with the mercury inserting method.

The best reaction results can be obtained with good reproducibility only when the oxide compositions have a surface area and a pore volume specified above. Catalysts having a surface area of less than 4 $m^2/g$ or a pore volume of less than 0.08 ml/g reduce the conversion of unsaturated aldehydes and the selectivity to unsaturated carboxylic acids. On the other hand, catalysts having a surface area of more than 20 $m^2/g$ or a pore volume of more than 0.5 ml/g increase the conversion of unsaturated aldehydes, but promote the formation of CO and $CO_2$, which in turn results in reduced selectivity to unsaturated carboxylic acids and their yields.

The oxide composition of this invention may contain at least one additional element selected from Si, Cr, Al, Ge, Ti, V, W, Bi, Nb, B, Ga, Pb, Sn, Co, Pd, As, Zr, Sb, Te, Fe, Ni, In, Cu, Ag, Mn, La, Nd, and Sm besides (1) P, (2) Mo and (3) X (preferably, thallium, potassium, rubidium, cesium, strontium, barium, zinc and cadmium). The incorporation of the additional elements is extremely effective for further enhancing the activity of the catalyst.

The P:Mo:X atomic ratio in the oxide composition of this invention is 0.1–8:12:0.01–10, preferably 0.2–7:12:0.05–8, more preferably 0.3–5:12:0.2–6. When the composition contains the additional element, the atomic ratio of Mo to at least one additional element is 12:0.1–12, preferably 12:0.1–10, more preferably 12:0.3–8.

The oxide composition catalyst of this invention may be regarded as a mixture of oxides of various elements or as an oxygen-containing compound of elements or mixtures thereof. Preferred oxide compositions are oxygen-containing compounds in which the essential ingredients, P, Mo and X, form an X element salt of phosphomolybdic acid, or oxide compositions containing the oxygen-containing compound.

The amount of oxygen in the oxide composition is determined by the valency of elements other than oxygen which are present in the composition.

The P-Mo-X oxide composition itself used for the preparation of the catalyst of this invention, whether in the form of powder or block, can be prepared by various methods known in the art, for example, an evaporative drying method, an oxide mixing method or a co-precipitation method. Starting materials of the elements used for preparing the oxide composition are not restricted to oxides, but may include any compounds which can be converted to oxides by calcination. Examples of these starting materials are salts (e.g., ammonium salts, nitrates or halides), free acids, acid anhydrides heteropolyacids containing molybdenum (e.g., phosphomybdic acid), and heteropolyacid salts (ammonium salts, or X or additional element salts of phosphomolybdic acid). The calcination treatment for the purpose of converting the catalyst materials to an oxide composition, or of activating the catalyst, or of increasing the physical strength of the catalyst is carried out usually at 250° to 700° C., preferably 350° to 600° C. Of desired, the calcination can be carried out at the above temperature after performing a primary calcination treatment at lower temperatures.

One example of a process for preparing the P-Mo-X oxide composition involves adding an aqueous solution containing X element or water-soluble compounds of additional elements to an aqueous solution containing ammonium molybdate, further adding an aqueous solution containing phosphoric acid, evaporating the solution to dryness with stirring, calcining the solid residue obtained, and if desired, pulverizing or powdering the resulting solid to suitable sizes.

The resulting oxide composition can be used directly when it has a shape desirable for use as a catalyst and the surface area and pore volume specified in the present invention. In order to prepare catalysts having the surface area and pore volume specified in the present invention with good reproducibility, it is preferred to use well-known methods for adjusting the surface area and pore size of catalysts irrespective of whether or not pelletized catalysts are to be made by using a molding machine. For example, an inert finely divided carrier is incorporated in the starting materials for the oxide composition, or in a powder of the oxide composition before its molding or in a powder of the solid residue (non-calcined) mentioned in the above example of catalyst preparation. Or there is added a substance which burns or volatilizes off at the time of calcining treatment in the preparation of the oxide composition catalyst thereby to form the desired pores in the catalyst, for example, albumine, stearic acid, an aggregate of cellulose crystallites, polyvinyl alcohol, or polyethylene glycol. Or a suitable catalyst carrier is selected. The method using the substance which burns or volatilizes off at the time of the calcination and forms the pores in the catalyst is a preferred one for adjusting the surface area and pore volume of the catalyst.

In particular, when this method is employed at the time of preparing pelletized catalysts by various molding machines, catalysts having sufficient physical strength can be obtained with good reproducibility. When the inert finely divided carrier is used, the preferred amount of the carrier is up to 50% by weight based on the uncalcined catalyst, and when the combustible or volatile substance is used, its preferred amount is up to 10% by weight based on the uncalcined catalyst. Preferably, these additives have a particle diameter of not more than 100 microns. The addition of these substances may also bring about an effect of increasing the activity of the catalyst. It is also possible to use the catalyst deposited on an inert carrier.

In the preparation of pelletized catalysts, it is preferred further to perform preliminary experiments regarding the molding pressure, the amount of extrusion, the water content of the catalyst, or the type of a binder, etc. according to the type of the molding machine. Useful molding methods include, for example, a tabletting method, an extruding method, a conical pan pelletizing method, or a tumbling granulation method (also called an inclined disc type granulation method).

We have found that the tumbling granulation method is especially preferred in order to prepare pelletized catalysts having the specific surface area and pore volume defined in the present invention with good reproducibility. The tumbling granulation method itself is already known as one technique of granulating a powdery material. When this method is applied to the preparation of the catalyst of this invention, spherical catalyst particles having the specified surface area and pore volume and high physical strength can be obtained easily by merely using water or ammonia water as a binder without particularly adding a substance that burns or volatilizes off at the time of calcination.

One example of catalyst preparation by the tumbling granulation method comprises feeding an unpelletized, uncalcined oxide composition or a starting catalyst composition (before being converted to an oxide composition) into a tumbling granulator, granulating it at an elevated temperature while spraying a binder such as water or ammonia water over it, withdrawing the granules grown to the desired size either batchwise or continuously, if desired drying the granules, and then calcining them.

In the present invention, the catalyst can be used as obtained, or as diluted with an inert finely divided carrier or supported on such a carrier. Examples of the carrier are silicon carbide, silica, α-alumina, diatomaceous earth, or graphite. When such a carrier is used, too, the surface area and pore volume of the catalyst are measured with respect to the final form of the catalyst (that is, the catalyst ready for use in reactions).

The catalyst of this invention is used for the preparation of unsaturated carboxylic acids such as acrylic acid or methacrylic acid by the catalytic vaporphase oxidation of unsaturated aldehydes such as acrolein or methacrolein with molecular oxygen. In this reaction, oxygen can be used as a source of molcular oxygen, but for commercial operations, the air is preferred. An inert diluent gas which does not affect the reaction, such as steam, nitrogen, carbon dioxide, helium, argon or saturated hydrocarbons, may be introduced into the reaction system as a diluent.

The preferred concentration of the unsaturated aldehyde in the starting feed gas is 1 to 25% by volume. The ratio of the unsaturated aldehyde to oxygen is suitably 1:0.1–25.0, preferably 1:0.1–20.0. The reaction temperature is 300° to 500° C., preferably 330° to 450° C. The contact time which gives favorable results is 0.1 to 20 seconds, preferably 0.1 to 15 seconds (based on 0° C., 1 atm.).

The reaction pressure is not particularly critical, but the operation can be carried out also at elevated pressures. Satisfactory results can be obtained by operating at atmospheric pressure or a slightly elevated pressure. The reaction apparatus may be of the fixed bed, fluidized bed or moving bed type. The reaction product can be collected by known general methods. For example, in order to separate and collect the desired unsaturated carboxylic acid, there can be employed a method which comprises condensing and liquefying the product by a condenser, or a method which involves using a solvent to collect the product.

The following Examples illustrate the present invention more specifically. In these examples, the conversion of the unsaturated aldehyde and the yield and selectivity of the unsaturated carboxylic acid were as defined below. All analyses were performed by means of gas chromatography. For simplicity, the indication of oxygen in the ingredients of the oxide composition catalyst was omitted.

$$\text{Conversion}(\%) = \frac{\left(\begin{array}{c}\text{Moles of the}\\\text{unsaturated}\\\text{aldehyde fed}\end{array}\right) - \left(\begin{array}{c}\text{Moles of the}\\\text{unreacted}\\\text{unsaturated}\\\text{aldehyde}\end{array}\right)}{\left(\begin{array}{c}\text{Moles of the unsaturated}\\\text{aldehyde fed}\end{array}\right)} \times 100$$

$$\text{Yield}(\%) = \frac{\left(\begin{array}{c}\text{Moles of the unsaturated}\\\text{carboxylic acid formed}\end{array}\right)}{\left(\begin{array}{c}\text{Moles of the unsaturated}\\\text{aldehyde fed}\end{array}\right)} \times 100$$

$$\text{Selectivity}(\%) = \frac{\text{Yield}}{\text{Conversion}} \times 100$$

EXAMPLE 1

A. Preparation of Catalyst ($P_2Mo_{12}Cs_2Cr_{1.5}$ catalyst, the figures indicating the atomic ratios of the elements)

(A-1) Ammonium molybdate (212 g) and 22.8 g of ammonium chromate were dissolved in 300 ml. of water by heating. Then, an aqueous solution of 23 g of 85% by weight pohosphoric acid in 50 ml. of water and an aqueous solution prepared by dissolving 39.0 g of cesium nitrate in 200 ml. of water by heating were added to the resulting solution. The mixed solution was evaporated to dryness with stirring. The resulting solid residue was thoroughly dried at 120° C. for 24 hours. A pre-product for obtaining a P-Mo-Cs-Cr oxide composition catalyst was thus prepared.

(A-2) Using the pre-product obtained in (A-1) above, $P_2Mo_{12}Cs_2Cr_{1.5}$ oxide catalysts in various forms were prepared by the following molding methods.

(1) Screening method

The pre-product was calcined in a muffle furnace at 480° C. for 16 hours, and sieved to a size of 4 to 8 mesh. (catalyst No. 1-1).

(2) Tabletting method

The pre-product was primarily calcined in a muffle furnace at 300° C. for 4 hours, and then pulverized to a size of 20 mesh or below. The pulverized product was mixed with 2% by weight of carbon powder as a lubricant, and the mixture was tabletted into tablets having a size of 5 mm in diameter and 5 mm in length. The tablets were calcined in a muffle furnace at 480° C. for 16 hours. (catalysts Nos. 1-2 and Cl-1).

(3) Extruding method

The pre-product was pulverized into a fine powder having a size of 40 mesh or below. Water was added in an amount of 10% by weight, and the mixture was thoroughly kneaded. The neaded mixture was extruded using a die plate with a diameter of 3 mm, and cut to a length of 4 to 8 mm using a cutter. The resulting pellets were dried at 120° C. for 3 hours, and then calcined in a muffle furnace at 480° C. for 16 hours. (catalysts Nos. 1-3, 1-4 and Cl-2).

(4) Conical pan pelletizing method

Pellets having a diameter of 3 mm and a length of 4 to 7 mm prepared by the same procedure as in (3) above were subjected to a conical pan pelletizer to form elliptic pellets having a size of 3 mm (short diameter)×5 mm (long diameter). The pellets were dried at 120° C. for 3 hours, and then calcined in a muffle furnace at 480° C. for 16 hours. (catalysts Nos. 1-5 and Cl-3)

(5) Tumbling granulation method

The pre-product was pulverized to a fine powder having a size of 40 mesh or below, and placed in a rotary disc type granular having a diameter of 20 cm and a depth of 10 cm. and inclined at an angle of 30°. While heating the powder at a temperature of about 70° C., a 28% aqueous solution of ammonia was added dropwise, and the granulator was rotated at a speed of 30 to 120 rpm to granulate the powder into spherical granules having a diameter of 5 mm. The granules were dried at 120° C. for 3 hours, and then calcined in a muffle furnace at 480° C. for 16 hours. (catalyst No. 1-6)

The surface areas and pore volumes of the catalysts obtained by the methods (1) to (5) were measured, and the results are shown in Table 1.

B. Reaction procedure

Each of the catalysts obtained by the methods described in A. above was subjected to the following activity test.

The catalyst (100 ml.) was packed in a stainless steel reaction tube having an inside diameter of 2.5 cm and a length of 60 cm, and heated in a metal bath. A feed gaseous mixture consisting of methacrolein, $O_2$, $N_2$ and $H_2O$ in a molar ratio of 1:1.5:17.5:10 was passed through the catalyst layer while adjusting the contact time to 1.8 seconds (based on 0° C., 1 atm.).

The results obtained are shown in Table 1. In the table, the reaction temperature refers to the maximum temperature of the catalyst layer at which the result obtained was the best.

C. Conclusion

The following conclusions can be drawn from the data shown in Table 1.

(1) The catalysts shown in Table 1 all consist of the same constituent ingredients. In spite of this those having the surface areas and pore volumes defined in the present invention exhibit superior results as catalysts for oxidizing unsaturated aldehydes.

(2) The catalysts having the surface areas and pore volumes defined by the present invention exhibit similar superior results irrespective of their shapes or the method of their preparation. Accordingly, catalysts having the surface areas and pore volumes defined in the present invention always give reaction results with good reproducibility.

The pre-product was pulverized into a fine powder having a size of 40 mesh or below, and then dried fully at 120° C. for 24 hours. The dried powder was well kneaded with 10% by weight of water, and the kneaded mixture was extruded at a rate of 10 cm per minute using a die plate with a diameter of 3 mm. At this time, heat was generated owing to the extrusion resistance, and the temperature of the die plate rose. Therefore, the die plate was cooled with water to maintain the die plate always at 40° C. The extrudate was cut to a size of 4 mm, dried at 120° C. for 3 hours, and then calcined in a muffle furnace at 480° C. for 16 hours. In this manner, four batches of catalyst were prepared independently from each other by the same procedure and under the same conditions.

(3) Tumbling granulation method

The pre-product was pulverized into a fine powder having a size of 40 mesh or below, and placed in a ro- Table 1

| Catalyst No. | Molding method | Pore volume (ml/g) | Surface area (m²/g) | Reaction temperature (°C.) | Conversion of methacrolein (%) | Yield (selectivity) of methacrylic acid (%) |
|---|---|---|---|---|---|---|
| Invention | | | | | | |
| 1-1 | Screening | 0.2448 | 15.2 | 398 | 81.5 | 53.7(65.9) |
| 1-2 | Tabletting | 0.1196 | 10.1 | 408 | 81.7 | 51.6(63.2) |
| 1-3 | Extruding | 0.1958 | 11.8 | 385 | 79.0 | 49.1(62.2) |
| 1-4 | Extruding | 0.1521 | 6.74 | 390 | 81.7 | 51.7(63.3) |
| 1-5 | Conical pan pelletizing | 0.1472 | 5.13 | 386 | 80.5 | 53.8(66.8) |
| 1-6 | Tumbling granulation | 0.1533 | 7.76 | 395 | 88.0 | 56.2(63.9) |
| Comparison | | | | | | |
| C1-1 | Tabletting | 0.0746 | 8.40 | 406 | 76.4 | 33.8(44.3) |
| C1-2 | Extruding | 0.0621 | 2.99 | 415 | 67.3 | 27.7(41.2) |
| C1-3 | Conical pan pelletizing | 0.0611 | 6.53 | 400 | 80.6 | 39.6(49.1) |

EXAMPLE 2

In order to examine the reproducibility of pelletized catalysts prepared by the tabletting method, extruding method and tumbling granulation method, several batches of catalysts were prepared by each of the molding methods by the same catalyst preparing and molding procedure under the same catalyst preparing and molding conditions (the batches were prepared independently from one another). The pore volumes and surface areas of the catalysts obtained were measured, and the catalysts were subjected to an activity test.

Specifically, four batches of catalyst were prepared from the pre-product described in Example 1, (A-1) by the same procedure in accordance with each of the following molding methods. All of these catalysts were $P_2Mo_{12}Cs_2Cr_{1.5}$ oxide compositions.

(1) Tabletting method

The pre-product was primarily calcined in a muffle furnace at 300° C. for 4 hours, and then pulverized to a size of 20 mesh or below. Carbon powder (2% by weight) was exactly added to the pulverized product, and they were thoroughly mixed to form a uniform mixture. The powdery mixture was formed into tablets having a diameter of 5 mm and a length of 5 mm by means of a tabletting machine so that the break strength became 19.0 Kg per unit area of the cross section of the catalyst. The tablets were calcined in a muffle furnace at 480° C. for 16 hours. In this manner, four batches of catalyst were prepared independently from one another by the same procedure and under the same conditions.

(2) Extruding method tary disc type granulator having a diamter of 20 cm and a depth of 10 cm and inclined at an angle of 30° C. while heating the powder at about 70° C., the granulator was rotated at a speed of 60 rpm. Water (6% by weight) was added dropwise to the powder to granulate it into spherical granules having a diameter of 5 mm. The granules were dried at 120° C. for 3 hours, and calcined in a muffle furnace at 480° C. for 16 hours. In this manner, four batches of catalyst were prepared independently from one another by the same procedure and under the same conditions.

100 ml. of each of the catalysts so prepared was subjected to the same activity test as in Example 1, B. The results are shown in Table 2.

As can be seen from Table 2, catalysts having the surface area and pore volume defined in the present invention have superior catalytic activity and give reaction results with good reproducibility.

In regard to the molding methods, the tumbling granulation method has been found to be best for preparing molded catalysts having the surface area and pore volume defined in this invention with good reproducibility. Furthermore, it can be seen that the tumbling granulation method can give catalysts which afford better reaction results than those prepared by the other molding methods. In contrast, when the tabletting and extruding methods are used, catalysts not having the surface area and pore volume defined in the present invention are formed in some batches in spite of the fact that they have been prepared by quite the same procedure and under quite the same conditions. Thus, these two methods are inferior to the tumbling granulation method when it is desired to obtain catalysts having supeior catalytic activity with good reproducibility.

lysts having the specified pore volume and surface area and sufficient strength with good reproducibility, and Table 2

| Molding method | | Batch No. | Pore volume (ml/g) | Surface area (m²/g) | Reaction temperature (°C.) | Conversion of methacrolein (%) | Yield (selectivity) of methacrylic acid (%) |
|---|---|---|---|---|---|---|---|
| | Comparison | 1 | 0.1290 | 3.71 | 401 | 79.3 | 45.7(57.6) |
| | | 2 | 0.0989 | 7.54 | 403 | 80.2 | 51.5(64.2) |
| Tabletting | Invention | 3 | 0.1187 | 8.46 | 405 | 73.4 | 50.9(69.3) |
| | Comparison | 4 | 0.1448 | 1.50 | 410 | 79.8 | 39.1(49.0) |
| | Invention | 1 | 0.1020 | 9.12 | 418 | 73.9 | 50.2(67.9) |
| | | 2 | 0.1122 | 8.35 | 396 | 74.5 | 49.1(65.9) |
| Extruding | Comparison | 3 | 0.0698 | 7.81 | 405 | 75.8 | 34.1(45.0) |
| | Invention | 4 | 0.1547 | 8.00 | 414 | 79.0 | 52.1(70.0) |
| | | 1 | 0.1431 | 8.41 | 390 | 86.2 | 56.1(65.1) |
| Tumbling granulation | Invention | 2 | 0.1507 | 9.32 | 3.83 | 83.6 | 54.8(65.6) |
| | | 3 | 0.1510 | 7.99 | 391 | 84.3 | 55.0(65.2) |
| | | 4 | 0.1428 | 8.67 | 398 | 86.3 | 56.4(65.4) |

EXAMPLE 3

As can be seen from the examples shown in Example 2, with the tableting method and extruding method, it is difficult to prescribe molding conditions for obtaining catalysts having the specified pore volume and surface area with good reproducibility. Even when such conditions can be set, the resulting catalysts somethimes do not fully meet the requirements of commercial catalysts in respect of their yield and strength.

The re-product prepared by the method described in Example 1, (A-1) was pulverized under the pulverizing conditions in the molding methods (2) to (5) given in Example 1, (A-2). One or more of 1% by weight of stearic acid, 1% by weight of albumin, 10% by weight of silic anhydride and 5% by weight of silicon carbide, each pulverized to a size of 30 microns or below, were added to the pulverized product so as to be uniformly distributed therein. Then, each of the mixtures was molded by each of the molding methods (2) to (5) so that it had sufficient strength. The molded product was calcined in a muffle furnace at 480° C. for 16 hours. Using the calcined catalysts, their activities were tested in the oxidation of methacrolein by the same method as described in Example 1, B. The results are shown in Table 3.

As can be seen from Table 3, the addition of these finely divided additives makes it possible to form catacan also bring about some increase in activity (the yield of methacrylic acid).

However, as can be seen from the comparisons, depending upon the molding conditions, the catalysts obtained do not have the specified pore volume and surface area, and the activity (the yield and selectivity of methacrylic acid) of such catalysts is poor. Thus, apparently, it can be concluded that the catalytic activity is not maintained by the additives, but it is maintained because the additives can give the specified pore volume and surface area. It can be appreciated therefore that no particular limitation is required with regard to the additives, but they can be any substances which form pores at the time of molding or calcination; and that, it is preferred to prescribe molding conditions by performing preliminary experiments.

Table 3

| | Catalyst No. | Molding method | Additive | Pore volume (ml/g) | Surface area (m²/g) | Reaction Temperature (°C.) | Conversion of methacrolein (%) | Yield (selectivity) of methacrylic acid (%) |
|---|---|---|---|---|---|---|---|---|
| | 3-1 | Tabletting | Silicic anhydride | 0.1100 | 6.61 | 400 | 79.9 | 50.0(62.6) |
| | 3-2 | Tabletting | Silicon carbide | 0.1213 | 6.80 | 405 | 82.3 | 51.1(62.1) |
| | 3-3 | Extruding | Silicic anhydride | 0.1327 | 7.58 | 415 | 81.3 | 52.9(65.1) |
| Invention | 3-4 | Extruding | Stearic acid | 0.1835 | 11.40 | 383 | 81.0 | 53.6(66.2) |
| | 3-5 | Conical pan pelletizing | Albumin | 0.1522 | 6.88 | 400 | 84.6 | 53.1(62.8) |
| | 3-6 | Tumbling granulation | Silicic anhydride | 0.2074 | 9.79 | 398 | 89.2 | 58.3(65.4) |
| | 3-7 | Tumbling granulation | Silicic anhydride & stearic acid | 0.1840 | 8.95 | 392 | 85.4 | 57.8(67.7) |
| Comparison | C3-1 | Tabletting | Silicon carbide | 0.0761 | 3.90 | 410 | 81.9 | 33.6(41.1) |
| | C3-2 | Extruding | Stearic acid | 0.0691 | 8.17 | 407 | 81.5 | 44.8(55.0) |

EXAMPLE 4

(a) $P_2Mo_{12}Cs_2Ba_1$ catalyst

Ammonium molybdate (212 g) was dissolved in 300 ml. of water by heating, and an aqueous solution prepared by dissolving 26.1 of barium nitrate in 200 ml. of water by heating was added to the solution. The mixture was stirred. Furthermore, an aqueous solution of 23 g of 85% by weight phosphoric acid in 50 ml. of water and an aqueous solution prepared by dissolving 39.0 g of cesium nitrate in 200 ml. of water by heating were added to the resulting solution. The mixed solution was evaporated to dryness with stirring. The resulting solid residue was fully dried at 120° C. for 24 hours to form a pre-product.

The pre-product was molded by the methods (3) and (5) described in Example 1, (A-2), and calcined in a muffle furnace at 450° C. for 16 hours. Thus, catalysts Nos. 4-1, 4-2 and C4-1 were prepared.

(b) $P_2Mo_{12}Tl_2Cr_{1.5}$ catalyst

Ammonium molybdate (212 g) and 22.8 g of ammonium chromate were dissolved in 300 ml. of water by heating, and an aqueous solution of 23 g of 85% by weight phosphoric acid in 50 ml. of water and an aqueous solution prepared by dissolving 53.3 g of thallium nitrate in 200 ml. of water by heating were added. The mixed solution was evaporated to dryness with stirring. The resulting solid residue was fully dried at 120° C. for 24 hours to form a pre-product. The pre-product was molded by the methods (2) and (5) described in Example 1. (A-2), and calcined in muffle furnace at 480° C. for 16 hours. Thus, catalysts Nos. 4-3, 4-4 and C4-2 were prepared.

(c) $P_2Mo_{12}Rb_2Cr_{1.5}$ catalyst

A pre-product was prepared in the same way as in (b) above except that 29.5 g of rubidium nitrate was used instead of the thallium nitrate. The pre-product was molded by the methods (3) and (5) described in Example 1, (A-2), and calcined in a muffle furnace at 480° C. for 16 hours. Thus, catalysts Nos. 4-5, 4-6 and C4-3 were prepared.

(d) $P_2Mo_{12}Cs_2V_1$ catalyst

A pre-product was prepared in the same way as in (a) above except that an aqueous solution prepared by dissolving 23.4 g of ammonium metavanadate in 200 ml. of a warm aqueous solution containing 35.1 g of oxalic acid was used instead of the aqueous solution of barium nitrate. The pre-product was molded by the methods (2), (3) and (5) described in Example 1, (A-2), and calcined in a muffle furnace at 430° C. for 16 hours. Thus, catalysts Nos. 4-7, 4-8, 4-9, C4-4 and C4-5 were prepared.

(e) $P_2Mo_{12}Ti_2V_1$ catalyst

A pre-product was prepared in the same way as in (d) above except that 53.3 g of thallium nitrate was used instead of the cesium nitrate. The pre-product was molded by the methods (2) and (4) described in Example 1, (A-2), and calcined in a muffle furnace at 430° C. for 16 hours. Thus, catalysts Nos. 4-10, 4-11 and C4-6 were prepared.

(f) $P_2Mo_{12}Cs_2Sr_{0.5}V_1$ catalyst

A pre-product was prepared in the same way as in (d) above except that an aqueous solution of 10.55 g of strontium nitrate in 200 ml. of water was further added. The pre-product was molded by the method (3) described in Example 1, (A-2), and calcined in a muffle furnace at 430° C. for 16 hours. Thus, catalysts Nos. 4-12 and C4-7 were prepared.

(g) $P_2Mo_{12}Cd_1Cr_{1.5}$ catalyst

A pre-product was prepared in the same way as in (b) above except that 30.8 g of cadmium nitrate was used instead of the thallium nitrate. The pre-product was molded by the methods (2) to (5) described in Example 1, (A-2), and calcined in a muffle furnace at 450° C. for 16 hours. Thus, catalysts Nos. 4-13, 4-14, 4-15, 4-16, C4-8, C4-9 and C4-10 were prepared.

The pore volumes and surface areas of the catalysts obtained above were measured, and the same activity test as in Example 1, B was performed. The results are shown in Table 4 (catalysts Nos. 4-1 to 4-16). For comparison, the results of an activity test of catalyst having pore volumes and surface areas outside the ranges specified in this invention are also shown (catalysts Nos. C4-1 to C4-10).

The results shown in Table 4 demonstrate that the catalysts having the surface areas and pore volumes specified in the present invention show reaction results with good reporducibility irrespective of the method of preparing the molded catalysts.

Table 4

| Catalyst (atomic ratio) | Catalyst No. | | Molding method | Pore volume (ml/g) | Surface area (m²/g) | Reaction temperature (°C.) | Conversion of methacrolein (%) | Yield (selectivity) of methacrylic Acid (%) |
|---|---|---|---|---|---|---|---|---|
| (a) $P_2Mo_{12}Cs_2Ba_1$ | Invention | 4-1 | Extruding | 0.2181 | 7.6 | 388 | 77.3 | 50.1 (64.8) |
| | | 4-2 | Tumbling granulation | 0.2433 | 8.2 | 390 | 80.8 | 52.3 (64.7) |
| | Comparison | C4-1 | Extruding | 0.0321 | 2.8 | 415 | 70.0 | 31.7 (45.3) |
| (b) $P_2Mo_{12}Ti_2Cr_{1.5}$ | Invention | 4-3 | Tabletting | 0.2165 | 13.6 | 405 | 81.3 | 53.6 (65.9) |
| | | 4-4 | Tumbling granulation | 0.2234 | 8.4 | 402 | 86.4 | 56.8 (65.7) |
| | Comparison | C4-2 | Tabletting | 0.0541 | 3.7 | 412 | 73.0 | 31.1 (42.6) |
| (c) $P_2Mo_{12}Rb_2Cr_{1.5}$ | Invention | 4-5 | Extruding | 0.1962 | 5.0 | 400 | 73.3 | 48.6 (66.3) |
| | | 4-6 | Tumbling granulation | 0.2140 | 6.3 | 397 | 78.6 | 51.8 (65.9) |
| | Comparison | C4-3 | Extruding | 0.0497 | 4.2 | 402 | 54.4 | 27.0 (49.6) |
| (d) $P_2Mo_{12}Cs_2V_1$ | Invention | 4-7 | Tabletting | 0.3541 | 12.9 | 389 | 85.1 | 64.9 (76.3) |
| | | 4-8 | Extruding | 0.3188 | 11.1 | 390 | 84.6 | 65.0 (76.8) |
| | | 4-9 | Tumbling granulation | 0.3200 | 14.6 | 385 | 89.9 | 69.2 (77.0) |
| | Comparison | C4-4 | Tabletting | 0.0503 | 8.4 | 400 | 75.0 | 44.5 (59.3) |
| | | C4-5 | Extruding | 0.0616 | 7.9 | 401 | 75.3 | 45.5 (60.4) |
| (e) $P_2Mo_{12}Tl_2V_1$ | Invention | 4-10 | Tabletting | 0.3163 | 10.5 | 400 | 80.5 | 61.3 (76.1) |
| | | 4-11 | Conical pan pelletizing | 0.2831 | 11.1 | 395 | 82.3 | 60.9 (74.0) |
| | Comparison | C4-6 | Tabletting | 0.4129 | 24.6 | 371 | 90.1 | 41.8 (46.4) |
| (f) $P_2Mo_{12}Cs_2Sr_{0.5}V_1$ | Invention | 4-12 | Extruding | 0.3100 | 9.6 | 406 | 87.9 | 70.0 (79.6) |
| | Comparison | C4-7 | Extruding | 0.0611 | 4.9 | 406 | 75.0 | 42.7 (56.9) |
| | Invention | 4-13 | Tabletting | 0.2000 | 8.3 | 388 | 56.6 | 37.6 (66.4) |
| | | 4-14 | Extruding | 0.1541 | 5.8 | 390 | 54.3 | 37.1 (68.3) |
| | | 4-15 | Conical pan pelletizing | 0.1972 | 6.4 | 390 | 56.4 | 37.5 (66.5) |
| (g) | | 4-16 | Tumbling | 0.2105 | 9.0 | 385 | 61.3 | 40.4 (65.9) |

Table 4-continued

| Catalyst (atomic ratio) | Catalyst No. | | Molding method | Pore volume (ml/g) | Surface area (m²/g) | Reaction temperature (°C.) | Conversion of methacrolein (%) | Yield (selectivity) of methacrylic Acid (%) |
|---|---|---|---|---|---|---|---|---|
| $P_2Mo_{12}Cd_1Cr_{1.5}$ | | | granulation | | | | | |
| | | C4-8 | Tabletting | 0.0405 | 2.0 | 410 | 32.3 | 15.2 (47.0) |
| | Comparison | C4-9 | Extruding | 0.0413 | 2.8 | 412 | 33.3 | 15.1 (45.3) |
| | | C4-10 | Conical pan pelletizing | 0.5246 | 22.1 | 354 | 56.8 | 24.0 (42.3) |

EXAMPLE 5

Using each of the catalysts Nos. 1-4 and 1-6 of Example 1 and the catalysts Nos. 4-1, 4-6, 4-8 and 4-10 of Example 4, the same reaction as in Example 1, B was repeated except that acrolein was used instead of the methacrolein, and a feed gaseous mixture conisting of acrolein, $O_2$, $N_2$ and $H_2O$ in a molar ratio of 1:1.5:8:9.5 was passed while adjusting the contact time to 1.2 seconds (based on 0° C., 1 atm.). The results are shown in Table 5.

For comparison, each of the catalysts No. C1-2 of Example 1 and the catalysts Nos. C4-1, C4-4, C4-5 and C4-6 of Example 4 was used in the above procedure. The results are also shown in Table 5.

Table 5

| Catalyst (atomic ratio) | | Catalyst No. | Molding method | Pore volume (ml/g) | Surface area (m²/g) | Reaction temperature (°C.) | Conversion of acrolein (%) | Yield (selectivity of acrylic acid (%) |
|---|---|---|---|---|---|---|---|---|
| $P_2Mo_{12}Cs_2Cr_{1.5}$ | Invention | 1-4 | Extruding | 0.1521 | 6.74 | 399 | 92.0 | 80.7 (87.7) |
| | | 1-6 | Tumbling granulation | 0.1533 | 7.76 | 395 | 95.8 | 84.5 (88.2) |
| | Comparison | C1-3 | Extruding | 0.0621 | 2.99 | 404 | 86.4 | 61.1 (70.7) |
| $P_2Mo_{12}Tl_2Cr_{1.5}$ | Invention | 4-1 | Tabletting | 0.2165 | 13.6 | 396 | 90.4 | 79.3 (87.7) |
| | Comparison | C4-1 | Tabletting | 0.0541 | 3.7 | 400 | 84.1 | 58.0 (69.0) |
| | Invention | 4-6 | Extruding | 0.3188 | 11.1 | 385 | 94.7 | 83.6 (88.3) |
| $P_2Mo_{12}Cs_2V_1$ | | | | | | | | |
| | Comparison | C4-4 | Extruding | 0.0616 | 7.9 | 385 | 90.0 | 61.2 (68.0) |
| $P_2Mo_{12}Tl_2V_1$ | Invention | 4-8 | Tabletting | 0.3163 | 10.5 | 390 | 95.0 | 83.2 (87.6) |
| | Comparison | C4-5 | Tabletting | 0.4129 | 24.6 | 381 | 97.3 | 59.1 (60.7) |
| $P_2Mo_{12}Cs_2Sr_{0.5}V_1$ | Invention | 4-10 | Extruding | 0.3100 | 9.6 | 387 | 96.2 | 85.9 (89.3) |
| | Comparison | C4-6 | Extruding | 0.0611 | 4.9 | 397 | 85.4 | 60.6 (71.0) |

What we claim is:

1. A process for preparing a spherical shape pelletized oxide catalytic composition having a high degree of reproducibility of catalytic activity for oxidizing an unsaturated aldehyde into an unsaturated carboxylic acid, said composition consisting essentially of (1) phosphorus, (2) molybdenum, (3) X in which X is at least one element selected from the group consisting of thallium and metals of Groups 1A and II of the periodic table and, optionally (4) Z in which Z is at least one element selected from the group consisting of silicon, chromium, aluminum, germanium, titanium, vanadium, tungsten, bismuth, niobium, boron, gallium, lead, tin, cobalt, palladium, arsenic, zirconium, antimony, iron, nickel, indium, copper, silver, manganese, lanthanum, neodymium, samarium and tellurium at an atomic ratio of P:Mo:X:Z of 0.1-8:12:0.01-10:0-12 and a surface area of 4 to 20m²/g and a pore volume of 0.08 to 0.5 ml/g, said catalyst composition being produced by tumbling granulation comprising the steps of:

feeding the unpelletized, uncalcined catalytic composition into a tumbling granulator;

granulating the composition at an elevated temperature while spraying a binder selected from the group consisting of water and ammonia water until granules of a predetermined size have formed;

withdrawing the granules of said predetermined size; and calcining said granules.

2. The process of claim 1 in which, in said tumbling granulation method, the granules withdrawn from the tumbling granulator are dried prior to being calcined.

3. The process of claim 1 in which an inert finely divided carrier diluent is added to said tumbling granulator with said unpelletized, uncalcined catalyst composition.

4. The process of claim 1 wherein the catalyst composition fed to the tumbling granulator is in the form of a fine powder having a size of 40 mesh or less.

5. The process of claim 1, wherein the atomic ratio of (1) phosphorus: (2) molybdenum: (3) X is 0.2-7:12:0.-05-8.

6. The process of claim 1, wherein the atomic ratio of (1) phosphorus: (2) molybdenum: (3) X is 0.3-5:12:0.2-6.

7. The process of claim 1, wherein the atomic ratio of molybdenum to said element Z is 12:0.1-12.

8. The process of claim 1, wherein the atomic ratio of molybdenum to said element Z is 12:0.3-8.

9. The process of claim 1, wherein said catalyst composition has a surface area of 4.5 to 15 m²/g and a pore volume of 0.09 to 0.35 ml/g.

10. The process of claim 1, wherein Z is absent.

* * * * *